United States Patent [19]
Tucker et al.

[11] Patent Number: 5,693,002
[45] Date of Patent: Dec. 2, 1997

[54] SEXUAL APPLIANCE HAVING A SUCTION DEVICE WHICH PROVIDES STIMULATION

[75] Inventors: Martin Tucker, Encino, Calif.; Fai Pang Lin, Koowloon, Hong Kong; Serafin Antonio Hernandez, Tarzana, Calif.

[73] Assignee: Topco Sales, San Fernando, Calif.

[21] Appl. No.: 714,210

[22] Filed: Sep. 16, 1996

[51] Int. Cl.$^6$ ................................................ A61F 5/00
[52] U.S. Cl. ................................................ 600/38
[58] Field of Search ........................ 600/38, 39, 41; 128/830, 832, 833, 842, 843, 844

[56] References Cited

FOREIGN PATENT DOCUMENTS 2207169  9/1972  Germany ........................ 600/38

*Primary Examiner*—Jennifer Bahr
*Assistant Examiner*—Rosiland Kearney
*Attorney, Agent, or Firm*—Oppenheimer Poms Smith

[57] ABSTRACT

A sexual appliance that includes a main body portion having an aperture adapted to receive the wearer's penis and a suction device associated with the main body portion and adapted to apply a suction force to a predetermined portion of the anatomy of the wearer's intercourse partner.

28 Claims, 4 Drawing Sheets

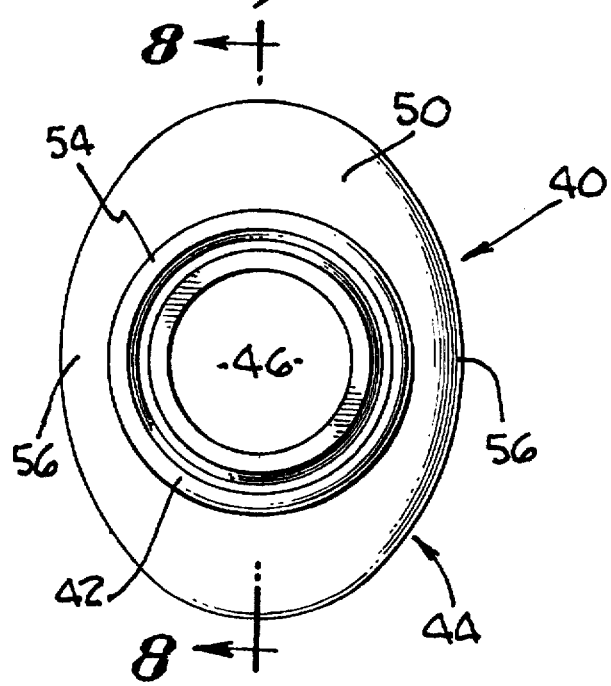
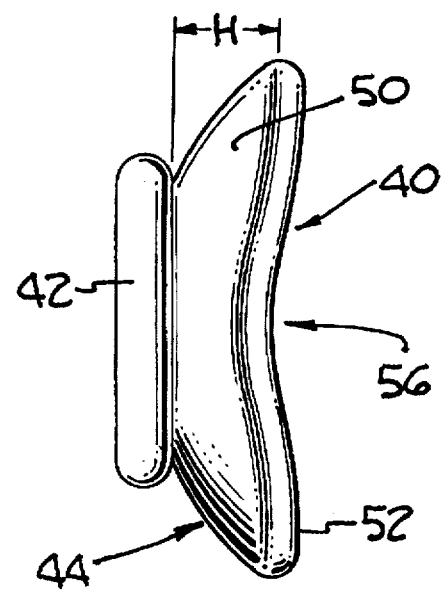
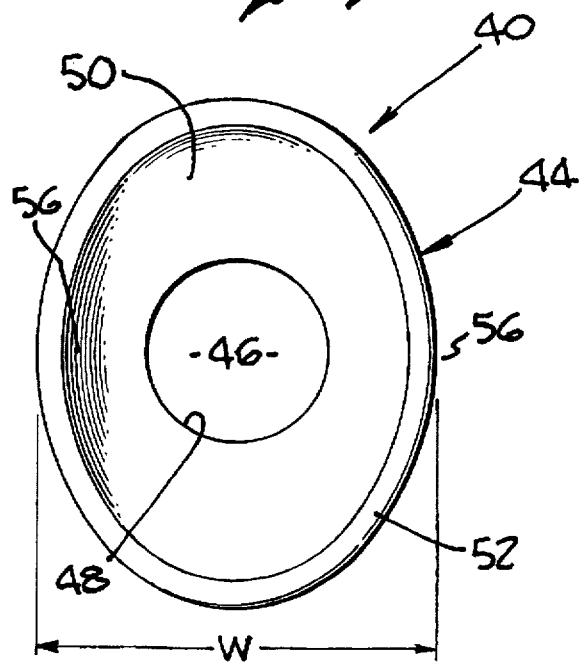
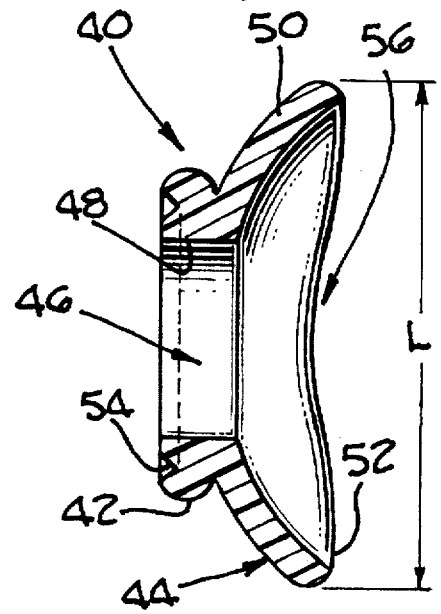

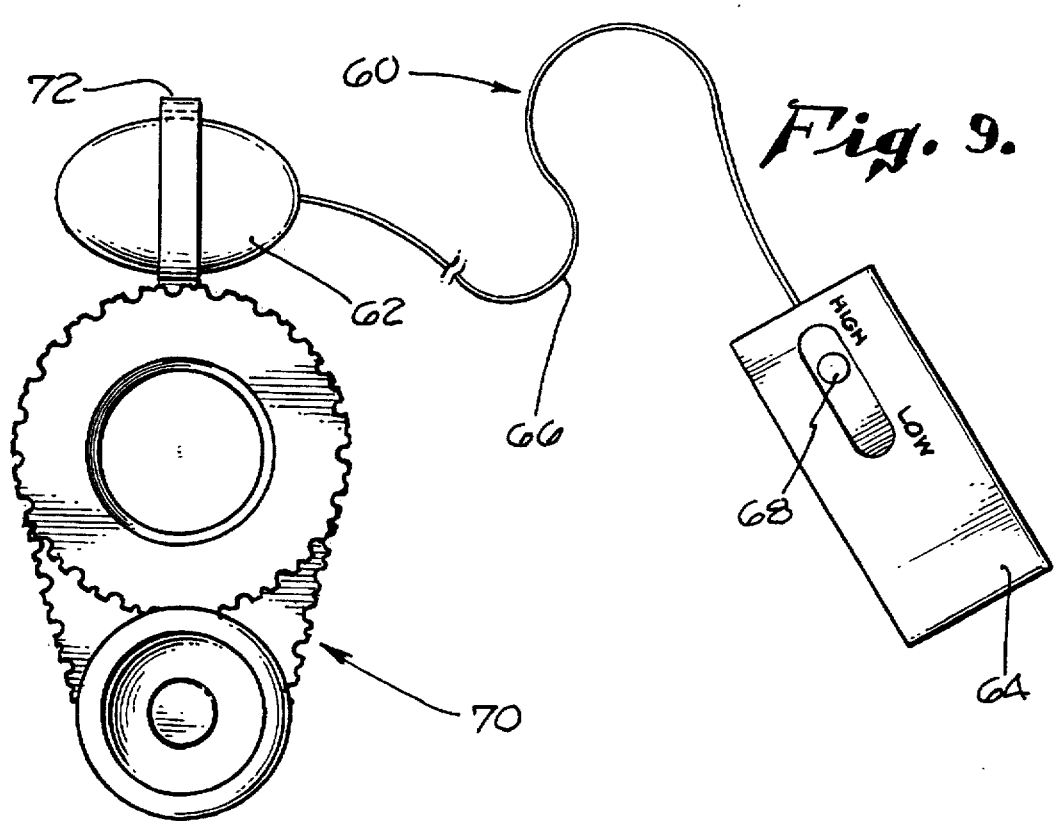
Fig. 9.
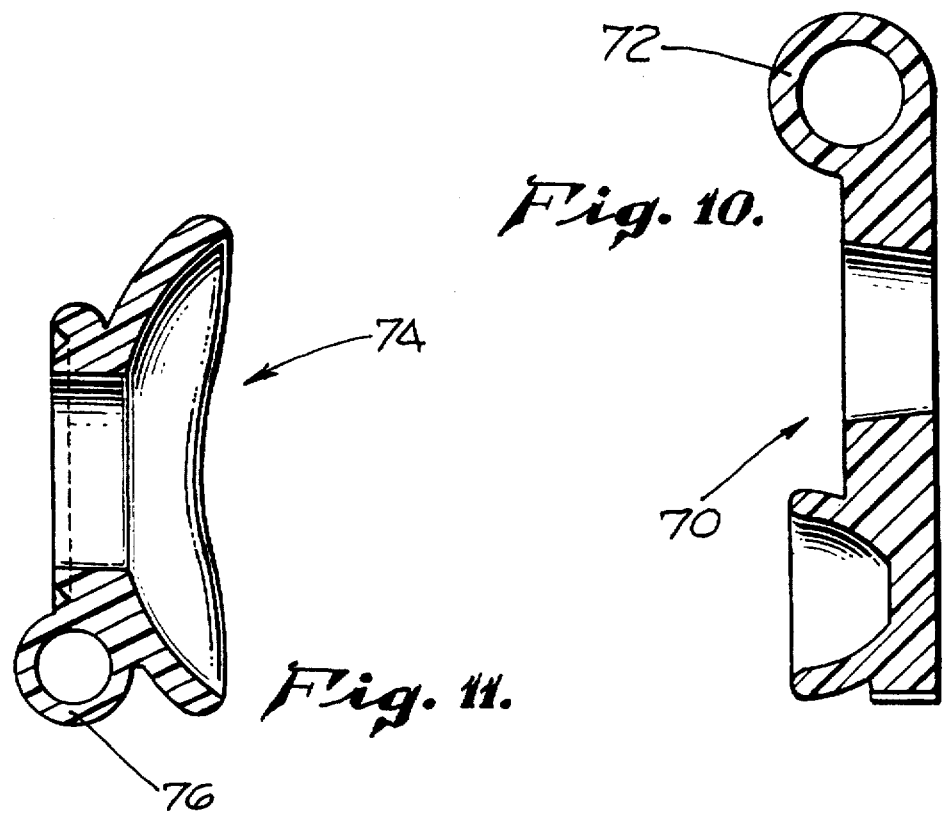
Fig. 10.
Fig. 11.

SEXUAL APPLIANCE HAVING A SUCTION DEVICE WHICH PROVIDES STIMULATION

BACKGROUND OF THE INVENTION

1. Field of Invention

The present invention is directed generally to the field of sexual appliances and, more particularly, to a sexual appliance which augments the sexual stimulation of the wearer's partner during intercourse.

2. Description of the Related Art

Over the years, a seemingly endless variety of so-called "marital aids" have been introduced into the marketplace. The primary purpose of a marital aid is to increase (or replace) the physical and psychological stimulation associated with sexual activity. By way of example, various lotions, creams, and sexual appliances (both mechanical and electro-mechanical) are readily available. The vast majority of sexual appliances consist of a smooth-edged contoured cylinder or a close replica of a human penis. Physical stimulation is derived from contact with the appliance. As such, a wide variety of exterior textures are available, as are the types of vibrations afforded by the electro-mechanical appliances.

Although generally useful, there are a number of shortcomings associated with the sexual appliances that have been introduced heretofore. For example, sexual appliances typically serve as a substitute for sexual intercourse, as opposed to merely enhancing the sexual experience. In addition, the range of sensations provided by known sexual appliances is somewhat limited. The sensations are similar to one another and are confined to those which may be produced solely through physical contact with the appliance.

SUMMARY OF THE INVENTION

The general object of the present invention is to provide a sexual appliance that is superior than those previously known in the art. In particular, one object of the present invention is to provide a sexual appliance that may be used to enhance, rather than replace, sexual intercourse. Another object of the present invention is to provide a sexual appliance which provides a sensation that is substantially different than those produced by known appliances.

In accordance with one aspect of the present invention, these and other objectives are accomplished by providing a sexual appliance which includes a main body portion having an aperture adapted to receive the wearer's penis and a suction device associated with the main body portion and adapted to apply a suction force to a predetermined portion of the anatomy of the wearer's intercourse partner. The suction force may, for example, be applied to specifically to the clitoral area, or to essentially the entire external portion of the female reproductive organs (i.e. the mons veneris, labia majora and minora, clitoris, meatus urinarius and orifice of the vagina) during intercourse. As a result, the present invention provides enhanced stimulation during intercourse. The present invention also provides a sensation that is substantially different than that provided by known sexual appliances, which rely solely on physical contact to produce the sensation.

Many other features and attendant advantages of the present invention will become apparent as the invention becomes better understood by reference to the following detailed description considered in conjunction with the accompanying drawings.

BRIEF DESCRIPTION OF THE DRAWINGS

Detailed description of the preferred embodiments of the invention will be made with reference to the accompanying drawings.

FIG. 5 is a rear elevation view of a sexual appliance in accordance with another preferred embodiment of the present invention.

FIG. 6 is a side elevation view of a sexual appliance in accordance with the preferred embodiment shown in FIG. 5.

FIG. 7 is a front elevation view of a sexual appliance in accordance with the preferred embodiment shown in FIG. 5.

FIG. 8 is a section view taken along line 8—8 in FIG. 5.

FIG. 9 is a front elevation view of a sexual appliance in accordance with another preferred embodiment of the present invention.

FIG. 10 is a side section view of the sexual appliance shown in FIG. 9.

FIG. 11 is a side section view of a sexual appliance in accordance with another preferred embodiment of the present invention.

DETAILED DESCRIPTION OF THE PREFERRED EMBODIMENT

Figure 1:
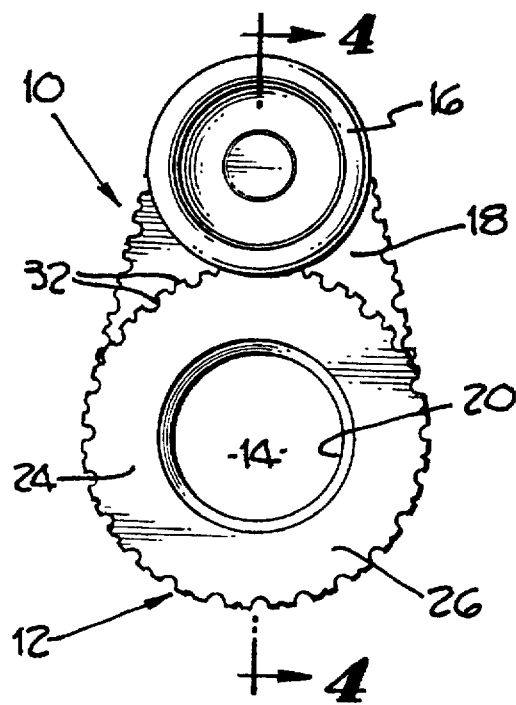
FIG. 1 is a front elevation view of a sexual appliance in accordance with one preferred embodiment of the present invention.
Figure 2:
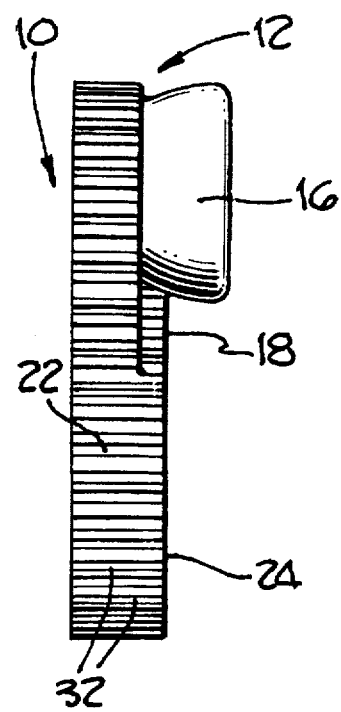
FIG. 2 is a side elevation view of a sexual appliance in accordance with the preferred embodiment shown in FIG. 1.

The following is a detailed description of the best presently known mode of carrying out the invention. This description is not to be taken in a limiting sense, but is made merely for the purpose of illustrating the general principles of the invention. The scope of the invention is defined solely by the appended claims.

As illustrated in FIGS. 1–4, a sexual appliance 10 in accordance with one preferred embodiment of the present invention includes a main body portion 12 having an aperture 14 formed therein. The aperture 14, which extends completely through the main body portion 12, is adapted to receive the penis of the wearer. To that end, the main body portion 10, at least in the area around the aperture 14, should be formed from a resilient material (discussed in detail below) that will provide a tight and secure fit. A suction device 16 is mounted on the main body portion 12. The exemplary suction device 16 is a suction cup with a circular cross-section. The suction cup should also be formed from a resilient material. The suction cup will form a substantially air-tight fit with a portion of the anatomy of the wearer's partner and produce a suction force as the cup is pulled away from the partner.

The size of the suction device 16 and its spacing from the aperture 14 may be used to facilitate the application of suction force to the clitoral area of the wearer's intercourse partner. In accordance with the exemplary embodiment shown in FIGS. 1–4, the distance between the center of the aperture 14 and the center of the suction device 16 is approximately 1.5 inches. With respect to the size of the suction device 16, the diameter "D" is approximately 1.5 inches, the depth "d" is approximately 0.5 inches and the height "H" (measured from the front surface 18 of the main body portion) is approximately 0.375 inches. In addition, the aperture 14 has an interior wall 20 that may be generally frusto-conically shaped, with a maximum diameter of approximately 1.125 inches and a minimum diameter of approximately 1.0 inch. As best seen in FIG. 4, the portion of the exemplary aperture 14 having the minimum diameter is adjacent to the rear surface 22 of the main body portion.

The exemplary appliance 10 shown in FIGS. 1–4 also includes an annularly-shaped member 24 located on the front surface 18 of the main body portion. The annularly-shaped member 24 extends forwardly from the front surface, but to a lesser extent than the suction device 16. Preferably, the annularly-shaped member 24 extends approximately 0.125 inches from the front surface 18. The center of the annularly-shaped member 24 forms part of the aperture 14 (note FIG. 4) and the portion of the aperture having the maximum diameter is adjacent to the forward surface 26 of the annularly-shaped member 24.

Figure 3:
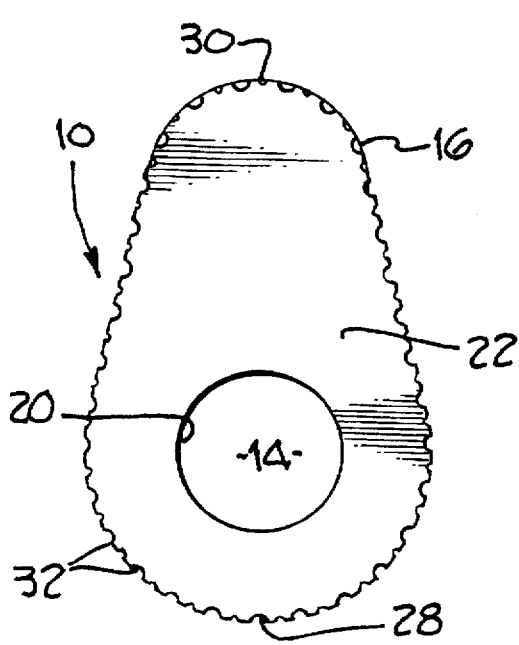
FIG. 3 is a rear elevation view of a sexual appliance in accordance with the preferred embodiment shown in FIG. 1.
Figure 4:
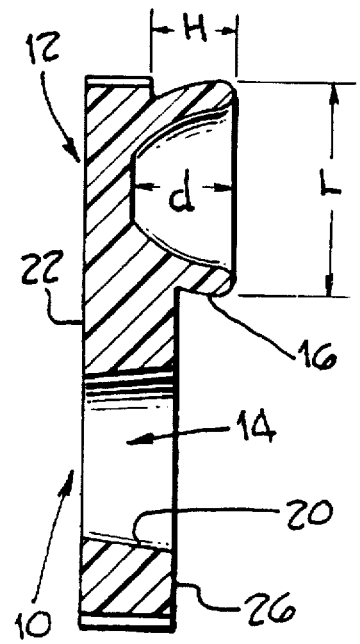
FIG. 4 is a section view taken along line 4—4 in FIG. 1.

As shown by way of example in FIGS. 1 and 3, the longitudinal ends 28 and 30 of the main body portion 12 may be curved. In the illustrated embodiment, the radius of curvature for the longitudinal end 28 is approximately 1.0 inch and the radius of curvature for the longitudinal end 30 is approximately 0.625 inches. Thus, the lateral extent of the first longitudinal end 28 is approximately 2.0 inches and the lateral extent of the second longitudinal end 30 is approximately 1.25 inches. In addition, the perimeter of the exemplary main body portion 12 and annularly-shaped member 24 include a plurality of ridges 32. The ridges are alternately relatively large and relatively small.

Another preferred embodiment of the present invention, generally represented by reference numeral 40, is illustrated in FIGS. 5–8. Exemplary sexual appliance 40 includes a main body portion 42 and a suction device 44. The main body portion 42 and suction device 44 include coaxial apertures which together form a single aperture 46 that is adapted to receive the penis of the wearer. The main body portion 42 and suction device 44 should be formed from a resilient material (discussed in detail below) that will provide a tight and secure fit. The exemplary suction device 44 is a suction cup with an elliptical cross-section.

The exemplary suction cup is sized so as to facilitate the application of suction force to the approximately the entire external portion of the reproductive organs of the wearer's intercourse partner. In accordance with the exemplary embodiment shown in FIGS. 5–8, the length (or major axis) "L" of the elliptical suction device 44 is approximately 2.875 inches and the width (or minor axis) "W" is approximately 2.25 inches. The maximum height "H" is approximately 0.75 inches. In addition, the aperture 46 has an interior wall 48 that is generally cylindrically-shaped and has a diameter of approximately 1.0 inch.

The exemplary main body portion 42 has substantially-ring shaped exterior. The rearward end of the main body portion 42 includes a channel 54 which increases the flexibility of the main body portion and, accordingly, the comfort of the wearer. The exemplary channel 54 is v-shaped, but the shape may be varied as desired in order to vary the amount of flexibility.

The suction device 44 includes a wall member 50 and a rim 52. In accordance with the preferred embodiment shown in FIGS. 5–8, the rim 52 is slightly depressed on opposing sides. Specifically, the rim 52 has a pair of slight depressions 56 along the sides which extend in approximately the same direction as the major axis. This configuration helps the wall member 50 conform to the shape of the anatomy of the wearer's partner. As a result, a substantially air-tight fit will be formed and a suction force will be generated as the suction device is pulled away from the partner.

With respect to materials and manufacturing, the present invention is preferably formed from an injection molded resilient, rubber-like material such as polyvinyl chloride. Not only does the resilient material provide for a tight and secure fit around the wearer's penis, but it also affords the suction devices with the flexibility necessary to form at least a substantially air-tight fit with the desired portion of the anatomy of the wearer's partner.

As shown by way of example in FIGS. 9 and 10, a vibrating device 60 may be used in conjunction with either of the preferred embodiments described above. The exemplary vibrating device 60 includes a relatively small (approximately two inches long and one inch in diameter) vibrating element 62 that is connected to a variable speed actuator 64 by a wire 66. The actuator 64 houses batteries and has a slidable speed control button 68. The vibrating element 62 may be supported on exemplary sexual appliances 70 (FIGS. 9 and 10) and 74 (FIG. 11) by support rings 72 and 76, respectively. A second support ring and vibrating device (not shown) may also be added to the other end of the embodiment shown in FIGS. 9 and 10. Here, both vibrating devices would be attached to a single actuator that has two speed control buttons. The support rings, which are formed from the same resilient material as the other portions of the appliances, have a diameter that is slightly less than that of the vibrating element 62. As a result, the support rings 72 and 76 stretch and apply a gripping force to the vibrating element when the vibrating element is inserted into the rings.

The exemplary device 70 shown in FIGS. 9 and 10 may be worn in many different ways. For example, oriented as shown in FIG. 9, and worn such that the wearer's penis extends through the device in the same direction as the suction cup, the vibrating element 62 will provide clitoral stimulation, while the suction cup provides suction-based stimulation to the perineum (the area between the vaginal area and the anus). If rotated 180 degrees, the vibrating element 62 would provide testicular stimulation, while the suction cup provides clitoral stimulation. Moreover, the vibrating element 62 also causes the entire sexual device (70 or 74) to vibrate, thereby providing additional stimulation.

Figure 12:
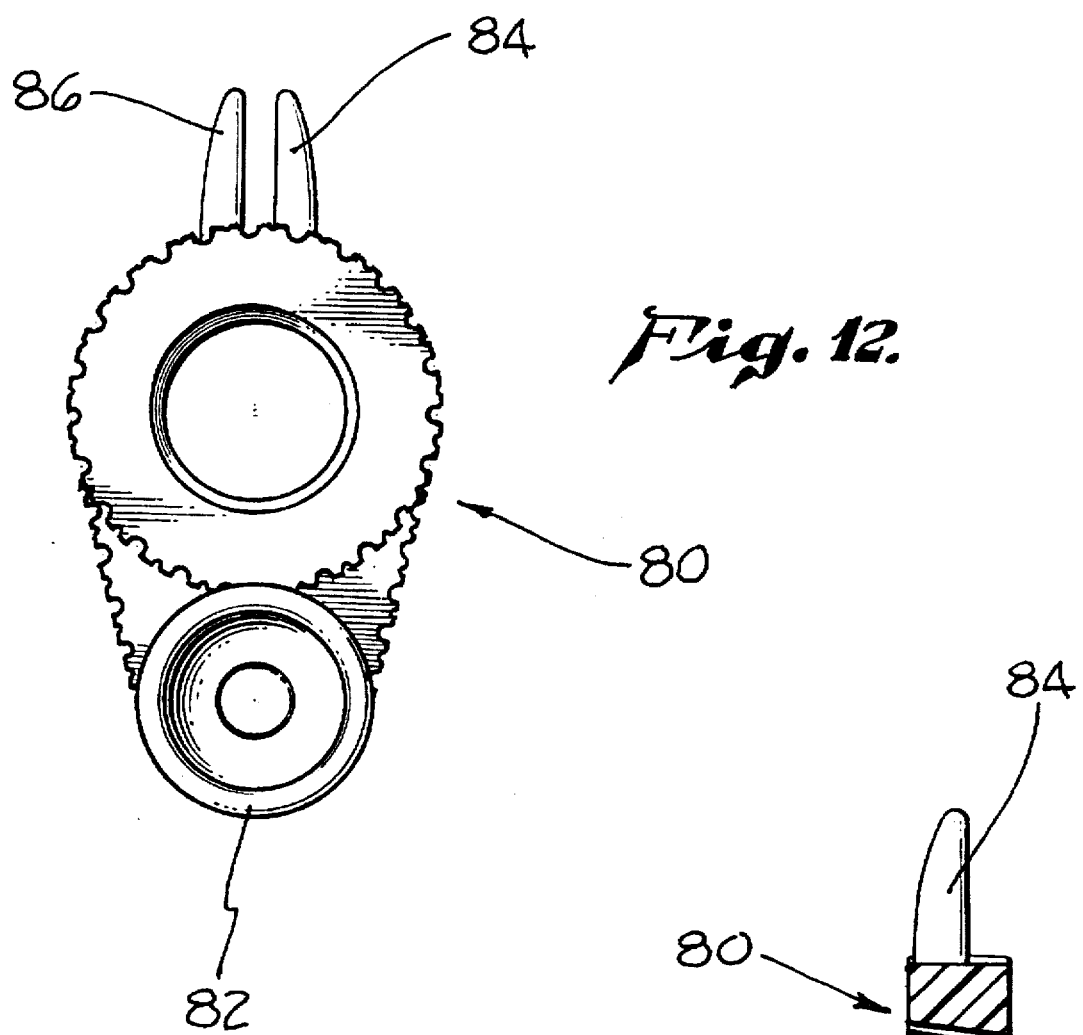
FIG. 12 is a front elevation view of a sexual appliance in accordance with another preferred embodiment of the present invention.
Figure 13:
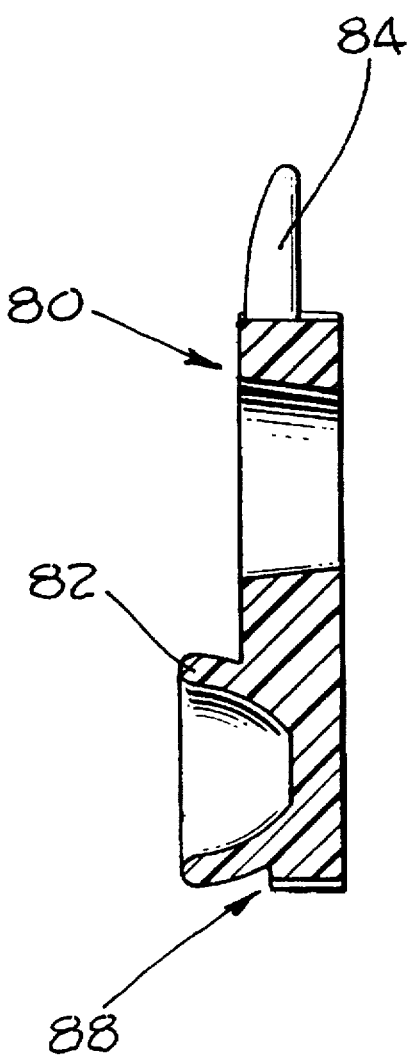
FIG. 13 is a side section view of the sexual appliance shown in FIG. 12.

Turning to FIGS. 12 and 13, a sexual appliance 80 in accordance with another preferred embodiment of the present invention a suction device 82 is provided at one end of the appliance 80 and a pair of stimulators 84 and 86 are provided at the other. A ring and vibrating element arrangement such as that described above (not shown) may be added to the appliance 80 at, for example, the location identified by reference numeral 88. The device shown in FIGS. 12 and 13 may also be worn in a variety of ways. For example, oriented as shown in FIG. 12, and worn such that the wearer's penis extends through the device in the same direction as the suction device 82, the device provides suction-based stimulation to the perineum and contact-based stimulation to the clitoral area. Rotating the device by 180 degrees will reverse these effects. The device may also be worn in the orientation shown in FIG. 12, but with the wearer's penis extending through the device in the direction opposite the suction device 82. So worn, suction-based stimulation will be provided to the wearer's testicles, while clitoral stimulation will be provided by the stimulators 84 and 86. The device may also be rotated 180 degrees when worn in this manner.

Although the present invention has been described in terms of the preferred embodiments above, numerous modifications and/or additions to the above-described preferred embodiments would be readily apparent to one skilled in the art. By way of example, but not limitation, the shape of the apertures may be modified and the surfaces thereof may be textured. The various dimensions specified above may be modified to suit particular needs, as may the shape of the suction devices and main body portions. Also, selected portions of the exemplary devices may be formed from a rigid material or a resilient material other than the resilient material described above. It is intended that the scope of the present invention extends to all such modifications and/or additions and that the scope of the present invention is limited solely by the claims set forth below.

What is claimed is:

1. A sexual appliance for use during intercourse, comprising:
   a unitary main body portion formed from resilient material, the main body portion having an aperture passing through the resilient material adapted to receive the penis of a wearer; and
   a suction device associated with the main body portion and adapted to apply a suction force to a predetermined portion of the anatomy of the wearer's intercourse partner.

2. A sexual appliance as claimed in claim 1, wherein the predetermined portion of the anatomy comprises at least a portion of the external portion of the female reproductive organs.

3. A sexual appliance as claimed in claim 1, wherein the resilient material comprises polyvinyl chloride.

4. A sexual appliance as claimed in claim 1, wherein the suction device comprises a generally cup-shaped member.

5. A sexual appliance as claimed in claim 1, wherein the main body portion comprises a generally circularly-shaped portion.

6. A sexual appliance as claimed in claim 1, wherein the aperture defines a center, the suction device defines a center, and the respective centers of the aperture and suction device are longitudinally spaced from one another by a predetermined distance.

7. A sexual appliance as claimed in claim 6, wherein the predetermined distance is such that the suction device will apply the suction force primarily to the clitoral area of the wearer's intercourse partner.

8. A sexual appliance as claimed in claim 6, wherein the main body portion includes a first curved longitudinal end defining a first predetermined lateral extent and a second curved longitudinal end defining a second predetermined lateral extent, the first predetermined lateral extent being substantially greater than the second predetermined lateral extent.

9. A sexual appliance as claimed in claim 8, wherein the aperture is substantially adjacent to the first curved longitudinal end.

10. A sexual appliance as claimed in claim 6, wherein the aperture defines a generally frusto-conical shape.

11. A sexual appliance as claimed in claim 6, wherein the main body portion defines an exterior having a plurality of ridges formed thereon.

12. A sexual appliance for use during intercourse, comprising:
    a main body portion defining an aperture adapted to receive the penis of a wearer and a front surface, the main body portion including a substantially annularly-shaped portion coaxial with the aperture, the substantially annularly-shaped portion extending outwardly from the front surface; and
    a suction device associated with the front surface of the main body portion and adapted to apply a suction force to a predetermined portion of the anatomy of the wearer's intercourse partner, the suction device extending outwardly from the front surface of the main body portion to a greater extent than the substantially annularly-shaped portion.

13. A sexual appliance as claimed in claim 6, wherein the suction device comprises a generally cup-shaped member.

14. A sexual appliance as claimed in claim 13, wherein the generally cup-shaped member defines a substantially circular cross-section.

15. A sexual appliance for use during intercourse, comprising:
    a main body portion defining an aperture adapted to receive the penis of a wearer; and
    a suction device associated with the main body portion and adapted to apply a suction force to a predetermined portion of the anatomy of the wearer's intercourse partner, the suction device defining an aperture, the respective apertures of the main body portion and the suction device being substantially coaxial.

16. A sexual appliance as claimed in claim 15, wherein the suction device comprises a generally cup-shaped member.

17. A sexual appliance as claimed in claim 16, wherein the generally cup-shaped member defines a substantially elliptical cross-section having a major axis and a minor axis.

18. A sexual appliance as claimed in claim 17, wherein the generally cup-shaped member comprises a wall member extending outwardly from main body portion, the wall member defines a rim, and the rim defines at least one depression extending in substantially the same direction as the major axis.

19. A sexual appliance as claimed in claim 15, wherein the generally cup-shaped member comprises a wall member extending outwardly from main body portion, the wall member defines a rim, and the rim defines at least one depression.

20. A sexual appliance as claimed in claim 15, wherein the predetermined portion of the anatomy comprises a substantial majority of the external portion of the female reproductive organs.

21. A sexual appliance as claimed in claim 15, wherein the main body portion comprises a substantially ring-shaped portion.

22. A sexual appliance as claimed in claim 15, wherein the main body portion defines first and second sides, the suction device is associated with the first side, and the second side includes a channel.

23. A sexual appliance as claimed in claim 1, further comprising:
    a vibration device secured to at least one of the main body portion and the suction device.

24. A sexual appliance as claimed in claim 1, wherein the main body portion defines a first end and a second end, the first and second ends being on substantially opposite sides of the aperture, and the suction device is located on the first end, the sexual appliance further comprising:
    at least one stimulator associated with the second end and extending outwardly therefrom.

25. A sexual appliance as claimed in claim 24, wherein the at least one stimulator comprises a pair of stimulators.

26. A sexual appliance as claimed in claim 24, wherein the suction device extends outwardly from the main body portion in a first predetermined direction and the at least one stimulator defines a generally curved shape with an end portion extending in a direction substantially corresponding to the first predetermined direction.

27. A sexual appliance as claimed in claim 6, further comprising:
    a vibration device secured to the exterior of at least one of the main body portion and the suction device.

28. A sexual appliance as claimed in claim 15, further comprising:
    a vibration device secured to the exterior of at least one of the main body portion and the suction device.

* * * * *